United States Patent [19]

Hall

[11] 4,275,154

[45] Jun. 23, 1981

[54] NUTRIENT MEDIUM

[75] Inventor: Michael J. Hall, Welwyn, England

[73] Assignee: Hoffmann-La Roche Inc., Nutley, N.J.

[21] Appl. No.: 139,530

[22] Filed: Apr. 11, 1980

[30] Foreign Application Priority Data

Apr. 27, 1979 [GB] United Kingdom ............... 14742/79
Feb. 21, 1980 [GB] United Kingdom ............... 5883/80

[51] Int. Cl.$^3$ .............................................. C12Q 1/18
[52] U.S. Cl. ...................................... 435/32; 435/253
[58] Field of Search .................. 435/32, 33, 253, 254, 435/255, 256

[56] References Cited

U.S. PATENT DOCUMENTS 3,043,751 7/1962 Goldman ............................... 435/32
3,936,355 2/1976 Lawson ................................ 435/253

*Primary Examiner*—Robert J. Warden
*Attorney, Agent, or Firm*—Jon S. Saxe; Bernard S. Leon; Frank P. Hoffman

[57] ABSTRACT

A nutrient medium is presented for the cultivation of microorganisms. The nutrient medium is used in the determination of activity of a therapeutically-active substance against an infective microorganism.

7 Claims, No Drawings

NUTRIENT MEDIUM

DESCRIPTION OF THE INVENTION

The present invention relates to a nutrient medium. More particularly, the invention is concerned with a nutrient medium for the cultivation of microorganisms and with the use of said nutrient medium in the determination of the activity of a therapeutically-active substance against an infective microorganism.

The nutrient medium provided by the present invention is a synthetic and fully reproducible nutrient medium which contains, per liter of distilled water, the following ingredients:

2.0–5.5 g of anhydrous disodium hydrogen phosphate,
0.0005–0.005 g of ferrous sulphate heptahydrate,
0.001–0.01 g of folic acid,
0.0005–0.005 g of zinc sulphate heptahydrate,
0.0005–0.005 g of manganese sulphate tetrahydrate,
0.0005–0.005 g of cupric sulphate pentahydrate,
0.0001–0.0005 g of D-biotin,
0.004–0.04 g of uracil,
0.004–0.04 g of guanine,
0.004–0.04 g of cytosine,
0.004–0.04 g of adenine,
0.001–0.01 g of calcium D-pantothenate,
0.001–0.01 g of nicotinamide,
0.001–0.01 g of pyridoxal hydrochloride,
0.0001–0.005 g of thiamine hydrochloride,
0.001–0.01 g of i-inositol,
0.0005–0.005 g of cyanocabalamin,
0.001–0.05 g of choline dihydrogen citrate,
0.1–0.4 g of glycine,
0.1–0.5 g of L-valine,
0.1–0.5 g of L-lysine hydrochloride,
0.1–0.5 g of L-leucine,
0.1–0.5 g of L-isoleucine,
0.1–0.5 g of L-threonine,
0.02–0.05 g of L-tryptophan,
0.05–0.3 g of L-tyrosine,
0.15–0.25 g of L-arginine,
0.025–0.2 g of L-histidine,
0.1–0.5 g of L-cystine,
0.01–0.2 g of L-methionine,
0.1–0.5 g of L-proline,
0.1–0.4 g of L-phenylalanine,
0.05–0.5 g of L-asparagine,
0.01–0.1 g of L-alanine,
0.01–0.1 g of L-serine,
0.1–1.0 g of L-glutamic acid,
0.1–1.0 g of magnesium glycerophosphate monohydrate,
0.05–0.5 g of calcium gluconate,
0.4–2.0 g of anhydrous potassium dihydrogen phosphate,
1.0–4.0 g of anhydrous D-glucose, and
0.25–2.0 g of sodium citrate dihydrate.

To the nutrient medium according to the present invention may be added (per liter of distilled water) one or more of the following additional ingredients:
up to 0.01 g of riboflavine phosphate,
up to 0.001 g of menadione,
up to 0.5 g of L-cysteine,
up to 0.3 g of L-aspartic acid,
up to 2 g of sodium chloride,
up to 2 g of anhydrous ammonium sulphate,
up to 2 g of sodium pyruvate.

The preferred nutrient medium provided by the present invention is obtainable by dissolving per liter of distilled water, the following ingredients:
about 4.750 g of anhydrous disodium hydrogen phosphate,
about 0.001 g of ferrous sulphate heptahydrate,
about 0.005 g of folic acid,
about 0.001 g of zinc sulphate heptahydrate,
about 0.001 g of manganese sulphate tetrahydrate,
about 0.001 g of cupric sulphate pentahydrate,
about 0.0003 g of D-biotin,
about 0.01 g of uracil,
about 0.01 g of guanine,
about 0.01 g of cytosine,
about 0.01 g of adenine,
about 0.003 g of calcium D-pantothenate,
about 0.003 g of nicotinamide,
about 0.003 g of pyridoxal hydrochloride,
about 0.0003 g of thiamine hydrochloride,
about 0.003 g of riboflavine phosphate,
about 0.005 g of i-inositol,
about 0.001 g of cyanocobalamin,
about 0.0005 g of menadione,
about 0.005 g of choline dihydrogen citrate,
about 0.15 g of L-aspartic acid,
about 0.2 g of glycine,
about 0.3 g of L-valine,
about 0.2 g of L-lysine hydrochloride,
about 0.3 g of L-leucine,
about 0.2 g of L-isoleucine,
about 0.2 g of L-threonine,
about 0.025 g of L-tryptophan,
about 0.1 g of L-tyrosine,
about 0.2 g of L-arginine,
about 0.05 g of L-histidine,
about 0.3 g of L-cysteine,
about 0.2 g of L-cystine,
about 0.025 g of L-methionine,
about 0.2 g of L-proline,
about 0.2 g of L-phenylalanine,
about 0.1 g of L-asparagine,
about 0.05 g of L-serine,
about 0.025 g of L-alanine,
about 0.5 g of L-glutamic acid,
about 0.2 g of magnesium glycerophosphate monohydrate,
about 0.1 g of calcium gluconate,
about 0.91 g of anhydrous potassium dihydrogen phosphate,
about 2 g of anhydrous D-glucose,
about 1 g of anhydrous ammonium sulphate,
about 0.5 g of sodium pyruvate, and
about 0.75 g of sodium citrate dihydrate.

It will, of course, be appreciated that the aforementioned ingredients which are defined as salts with specified acids or bases can be replaced by the equivalent amount of the free base or acid or by the equivalent amount of a salt with a different acid or base. Further, an ingredient specified as a free base or a free acid can be present in the form of an appropriate salt with an acid or base, respectively. Yet again, an ingredient specified as a hydrate can be present in anhydrous form or in the form of a different hydrate which may be available.

The nutrient medium provided by the present invention can also be in the form of a gel formed with a gelling agent. The gelling agent can be any conventional gelling agent such as gelatin, silica gel, an agar, a mixture of a carboxyalkylcellulose and carrageenan etc.

In a preferred aspect, the present nutrient media are gelled with an agar or a mixture of carboxymethylcellulose and carrageenan.

The nutrient medium provided by the present invention can be manufactured, for example, by mixing together the dry ingredients referred to earlier and then dissolving the dry mixture obtained in the requisite amount of distilled water.

The order in which the ingredients is mixed together is not critical. However, it has been found to be convenient to first provide the following ingredient/mixtures in finely divided form:

(I) Anhydrous disodium hydrogen phosphate.

(II) Mixture of ferrous sulphate heptahydrate, folic acid, zinc sulphate heptahydrate, manganese sulphate tetrahydrate, cupric sulphate pentahydrate, D-biotin, uracil, guanine, cytosine, adenine, calcium D-pantothenate, nicotinamide, pyridoxal hydrochloride, thiamine hydrochloride, riboflavine phosphate (when present), i-inositol, cyanocobalamin, menadione (when present) and choline dihydrogen citrate.

(III) Mixture of L-aspartic acid (when present), glycine, L-valine, L-lysine hydrochloride, L-leucine, L-isoleucine, L-threonine, L-tryptophan-L-tyrosine, L-arginine, L-histidine, L-cysteine (when present), L-cystine, L-methionine, L-proline, L-phenylalanine, L-asparagine, L-serine, L-alanine, L-glutamic acid, magnesium glycerophosphate monohydrate and calcium gluconate.

(IV) Mixture of anhydrous potassium dihydrogen phosphate, D-glucose, sodium chloride (when present), anhydrous ammonium sulphate (when present), sodium pyruvate (when present) and sodium citrate dihydrate.

The production of the final dry mixture from I, II, III and IV hereinbefore is conveniently carried out by mixing II with I, the latter suitably being added portionwise. III is added to the resulting mixture and, after further mixing, IV is added. After further mixing, the final dry mixture is produced. This mixture is then dissolved in distilled water and the resulting medium is sterilised in a conventional manner; for example, by autoclaving or by micropore filtration.

The nutrient medium provided by the present invention possesses, inter alia, the following advantages:

(a) It can readily be prepared from ingredients having a fine particle size and improved dissolution properties compared to complex sensitivity testing media such as Mueller-Hinton agar, Diagnostic Sensitivity Test agar (Oxoid) and Isosensitest agar (Oxoid).

(b) It has excellent optical clarity and is free from precipitate, thus making it especially suitable for use in automatic instruments relying on light transmittance.

(c) It is prepared from a single powdered formulation, not requiring additives except those used in current practice.

(d) It is suitable for the growth of all common bacteria which cause urinary tract infection, gastric infection, respiratory tract infection and soft tissue infection, including anaerobes.

(e) It is suitable for use in the assay of sulphonamides, sulphonamide/potentiator compositions, D-cycloserine, tetracycline, phosphonopeptides (e.g. alafosfalin and analogues thereof such as, for example, those described in British Pat. No. 1,533,239), mecillinam, aminoglycosides etc.

(f) It has an improved buffering capacity compared with most complex sensitivity testing media.

(g) The ionic content is such that conductivity and osmolality is closer to physiological conditions than in the case of conventional complex sensitivity testing media.

(h) With slight modifications the present medium can be altered to become both selective and differential such as, for example, in the case of the present medium/MacConkey's medium or the present medium/Hektoen and Enteric agar.

As mentioned earlier, this invention is also concerned with the use of the medium provided by the present invention in determining the activity of a therapeutically-active substance against an infective microorganism. Thus, according to the invention, the medium can be inoculated with such a microorganism, an appropriate amount of the therapeutically-active substance can be applied, the medium can then be incubated at a suitable temperature (e.g. 35°–38° C.) for a suitable time (e.g. 12–24 hours) and the activity of the therapeutically-active substance against the infective microorganism can then be determined by reference to the density in broth or diameter of the inhibition zone which is formed on the solid medium or in the presence or absence of growth on agar incorporating varying concentrations of the test substance.

EXAMPLE 1

This Example illustrates the preparation of a nutrient medium provided by the invention:

475 g of anhydrous disodium hydrogen phosphate are provided in sieved form (710 micron; 22 mesh).

0.1 g of ferrous sulphate heptahydrate, 0.5 g of folic acid, 0.1 g of zinc sulphate heptahydrate, 0.1 g of manganese sulphate tetrahydrate, 0.1 g of cupric sulphate pentahydrate, 0.03 g of D-biotin, 1.0 g of uracil, 1.0 g of guanine, 1.0 g of cytosine, 1.0 g of adenine, 0.3 g of calcium D-pantothenate, 3.0 g of nicotinamide, 0.3 g of pyridoxal hydrochloride, 0.03 g of thiamine hydrochloride, 0.3 g of riboflavine phosphate, 0.5 g of i-inositol, 0.1 g of cyanocobalamin, 0.05 g of menadione and 0.5 g of choline dihydrogen citrate are finely powdered and mixed using a pestle and mortar with an equal amount of the anhydrous disodium hydrogen phosphate. An approximately equal amount of the anhydrous disodium hydrogen phosphate is then added and the resulting mixture is further ground, mixed and subsequently passed through a 150 micron (100 mesh) sieve. The remaining anhydrous disodium hydrogen phosphate is added and the mixture obtained is mixed in a small tumble mixing drum.

15.0 g of L-aspartic acid, 20.0 g of glycine, 30.0 g of L-valine, 20.0 g of L-lysine hydrochloride, 30.0 g of L-leucine, 20.0 g of L-isoleucine, 20.0 g of L-threonine, 2.5 g of L-tryptophan, 10.0 g of L-tyrosine, 20.0 g of L-arginine, 5.0 g of L-histidine, 30.0 g of L-cysteine, 20.0 g of L-cystine, 2.5 g of L-methionine, 20.0 g of L-proline, 20.0 g of L-phenylalanine, 10.0 g of L-asparagine, 5.0 g of L-serine, 2.5 g of L-alanine, 50.0 g of L-glutamic acid, 20.0 g of magnesium glycerophosphate monohydrate and 10.0 g of calcium gluconate are mixed and passed through a 710 micron (22 mesh) sieve. The sieved mixture is blended for 3 minutes using a medium size tumble mixing drum. The mixture prepared as described in the preceding paragraph is now added and the resulting mixture is mixed for a further 3 minutes.

The following ingredients, are provided in sieved form (710 micron; 22 mesh): 91.0 g of anhydrous potassium dihydrogen phosphate, 200.0 g of anhydrous D-glucose, 100.0 g of anhydrous ammonium sulphate, 50.0 g of sodium pyruvate and 75.0 g of sodium citrate dihydrate. These sieved ingredients are added to the mixture prepared as described in the preceding paragraph and the resulting mixture is tumbled for 3 minutes. It is then passed through an Apex mill (hammers forward) fitted with a 0.015 inch type TE 015 screen (round hole). Finally, the milled mixture is blended for 5 minutes in a tumble mixing drum.

The appropriate amount of the final mixture obtained is dissolved in 100 liters of distilled or deionised water and the resulting solution is sterilised by autoclaving at 121° C. for 15–20 minutes.

EXAMPLE 2

Table I hereinafter shows the zone diameters (in mm) obtained by challenging representative microorganisms with various antibacterial agents on a nutrient medium provided by this invention (RST) and two commercially available media (DST and ISO). In this Table, RST = Medium provided by the present invention and prepared according to Example 1, but gelled with Oxoid bacteriological agar No. 1 (10 g per liter);
DST = Diagnostic Sensitivity Test agar (Oxoid);
ISO = Isosensitest agar (Oxoid);
In = Inactive on this medium;
O = No visible zone.

TABLE I

| | Zone diameters (mm) | | | | | | | | |
|---|---|---|---|---|---|---|---|---|---|
| | Klebsiella aerogenes | | | Streptococcus pneumoniae | | | Staphylococcus aureus | | |
| Disc content | RST | DST* | ISO | RST* | DST* | ISO* | RST | DST* | ISO |
| Sulphamethoxazole (100 μg) | 25 | 25 | 25 | 29 | 30 | 31 | 31 | 32 | 31 |
| Erythromycin (10 μg) | 0 | 0 | 0 | 33 | 30 | 31 | 29 | 28 | 28 |
| Alafosfalin (10 μg) | 18 | In | In | 0 | In | In | 10 | In | In |
| Gentamicin (10 μg) | 20 | 20 | 20 | 0 | 0 | 0 | 30 | 26 | 27 |
| Tetracycline (25 μg) | 0 | 0 | 0 | 35 | 34 | 34 | 34 | 32 | 32 |
| Penicillin (1.5 μg) | 0 | 0 | 0 | 40 | 38 | 39 | 16 | 18 | 17 |
| Mecillinam (25 μg) | 31 | 28 | 29 | 28 | 26 | 27 | 21 | 21 | 21 |

*Addition of 6–8% lysed horse blood.

EXAMPLE 3

Table II hereinafter shows the minimum inhibitory concentration (MIC) in micrograms per ml obtained by dissolving appropriate amounts of the specified antibiotics in the nutrient medium of the present invention (RST) and two commercially available media (DST and ISO) and subsequently inoculating either the broth or the agar surface with the specified microorganism.

TABLE II

| | MIC (μg/ml) | | | | | | | | | | | |
|---|---|---|---|---|---|---|---|---|---|---|---|---|
| | Klebsiella aerogenes | | | Streptococcus pneumoniae | | | Staphylococcus aureus | | | E. coli | | |
| Antibiotic | RST | DST | ISO | RST | DST | ISO | RST | DST | ISO | RST | DST | ISO |
| Penicillin | >256 | >256 | >256 | 0.03 | 0.03 | 0.03 | 0.03 | 0.03 | 0.03 | >128 | >128 | >128 |
| Erythromycin | >256 | >256 | >256 | 0.03 | 0.03 | 0.03 | 0.03 | 0.03 | 0.03 | 128 | 64 | 64 |
| Tetracycline | 1 | 1 | 2 | 0.25 | 0.25 | 0.5 | 0.06 | 0.12 | 0.25 | 2 | 1 | 1 |
| Sulphamethoxazole | 8 | 8 | 8 | 4 | 4 | 4 | 8 | 8 | 8 | 8 | 8 | 8 |
| Centamycin | 2 | 2 | 2 | 32 | 16 | 16 | 0.06 | 0.06 | 0.06 | 2 | 1 | 0.5 |
| D-Cycloserine | >128 | >128 | >128 | NT | NT | NT | 2 | 32 | 32 | >128 | >128 | >128 |
| Alafosfalin | 1 | >256 | >256 | >128 | >256 | >256 | 4 | >256 | >256 | 1 | >256 | >256 |

NT = Not tested

What is claimed:
1. A nutrient medium the ingredients of which are dissolved in water, comprising per liter of water from about:
2.0 to 5.5 g of anhydrous disodium hydrogen phosphate,
0.0005 to 0.005 g of ferrous sulphate heptahydrate,
0.001 to 0.01 g of folic acid,
0.0005 to 0.005 g of zinc sulphate heptahydrate,
0.0005 to 0.005 g of manganese sulphate tetrahydrate,
0.0005 to 0.005 g of cupric sulphate pentahydrate,
0.0001 to 0.0005 g of D-biotin,
0.004 to 0.04 g of uracil,
0.004 to 0.04 g of guanine,
0.004 to 0.04 g of cytosine,
0.004 to 0.04 g of adenine,
0.001 to 0.01 g of calcium D-pantothenate,
0.001 to 0.01 g of nicotinamide,
0.001 to 0.01 g of pyridoxal hydrochloride,
0.0001 to 0.005 g of thiamine hydrochloride,
0.001 to 0.01 g of i-inositol,
0.0005 to 0.005 g of cyanocobalamin,
0.001 to 0.05 g of choline dihydrogen citrate,
0.1 to 0.4 g of glycine,
0.1 to 0.5 g of L-valine,
0.1 to 0.5 g of L-lysine hydrochloride,
0.1 to 0.5 g of L-leucine,
0.1 to 0.5 g of L-isoleucine,
0.1 to 0.5 g of L-threonine,
0.02 to 0.05 g of L-tryptophan,
0.05 to 0.3 g of L-tyrosine,
0.15 to 0.25 g of L-arginine,

0.025 to 0.2 g of L-histidine,
0.1 to 0.5 g of L-cystine,
0.01 to 0.2 g of L-methionine,
0.1 to 0.5 g of L-proline,
0.1 to 0.4 g of L-phenylalanine,
0.05 to 0.5 g of L-asparagine,
0.01 to 0.1 g of L-serine,
0.01 to 0.1 g of L-alanine,
0.1 to 1.0 g of L-glutamic acid,
0.1 to 1.0 g of magnesium glycerophosphate monohydrate,
0.05 to 0.5 g of calcium gluconate,
0.4 to 2.0 g of anhydrous potassium dihydrogen phosphate,
1.0 to 4.0 g of anhydrous D-glucose, and
0.25 to 2.0 g of sodium citrate dihydrate.

2. The nutrient of claim 1 wherein the following ingredients are present:
up to about 0.01 g of riboflavin phosphate,
up to about 0.001 g of menadione,
up to about 0.5 g of L-cysteine,
up to about 0.3 g of L-aspartic acid,
up to about 2 g of sodium chloride,
up to about 2 g of anhydrous ammonium sulphate,
up to about 2 g of sodium pyruvate.

3. A nutrient medium, the ingredients of which are dissolved in water, comprising per liter of water:
about 4.750 g of anhydrous disodium hydrogen phosphate,
about 0.001 g of ferrous sulphate heptahydrate,
about 0.005 g of folic acid,
about 0.001 g of zinc sulphate heptahydrate,
about 0.001 g of manganese sulphate tetrahydrate,
about 0.001 g of cupric sulphate pentahydrate,
about 0.0003 g of D-biotin,
about 0.01 g of uracil,
about 0.01 g of guanine,
about 0.01 g of cytosine,
about 0.01 g of adenine,
about 0.003 g of calcium D-pantothenate,
about 0.003 g of nicotinamide,
about 0.003 g of pyridoxal hydrochloride,
about 0.0003 g of thiamine hydrochloride,
about 0.003 g of riboflavine phosphate,
about 0.005 g of i-inositol,
about 0.001 g of cyanocobalamin,
about 0.0005 g of menadione,
about 0.005 g of choline dihydrogen citrate,
about 0.15 g of L-aspartic acid,
about 0.2 g of glycine,
about 0.3 g of L-valine,
about 0.2 g of L-lysine hydrochloride,
about 0.3 g of L-leucine,
about 0.2 g of L-isoleucine,
about 0.2 g of L-threonine,
about 0.025 g of L-tryptophan,
about 0.1 g of L-tyrosine,
about 0.2 g of L-arginine,
about 0.05 g of L-histidine,
about 0.3 g of L-cysteine,
about 0.2 g of L-cystine,
about 0.025 g of L-methionine,
about 0.2 g of L-proline,
about 0.2 g of L-phenylalanine,
about 0.1 g of L-asparagine,
about 0.05 g of L-serine,
about 0.025 g of L-alanine,
about 0.5 g of L-glutamic acid,
about 0.2 g of magnesium glycerophosphate monohydrate,
about 0.1 g of calcium gluconate,
about 0.91 g of anhydrous potassium dihydrogen phosphate,
about 2 g of anhydrous D-glucose,
about 1 g of anhydrous ammonium sulphate,
about 0.5 g of sodium pyruvate, and
about 0.75 g of sodium citrate dihydrate.

4. The nutrient medium of claim 3 wherein the composition is in the form of a gel.

5. The nutrient medium of claim 4 wherein the gel is formed by a gelling agent selected from the group consisting of an agar or a mixture of a carboxyalkylcellulose and carrageenan.

6. The nutrient medium of claim 5 wherein the carboxyalkylcellulose is carboxymethylcellulose.

7. A method of determining the activity of a therapeutically active substance against an infective microorganism which comprises
(A) inoculating with an infective microorganism a nutrient medium comprising per liter of water
2.0–5.5 g of anhydrous disodium hydrogen phosphate,
0.0005–0.005 g of ferrous sulphate heptahydrate,
0.001–0.01 g of folic acid,
0.0005–0.005 g of zinc sulphate heptahydrate,
0.0005–0.005 g of manganese sulphate tetrahydrate,
0.0005–0.005 g of cupric sulphate pentahydrate,
0.0001–0.0005 g of D-biotin,
0.004–0.04 g of uracil,
0.004–0.04 g of guanine,
0.004–0.04 g of cytosine,
0.004–0.04 g of adenine,
0.001–0.01 g of calcium D-pantothenate,
0.001–0.01 g of nicotinamide,
0.001–0.01 g of pyridoxal hydrochloride,
0.0001–0.005 g of thiamine hydrochloride,
0.001–0.01 g of i-inositol,
0.0005–0.005 g of cyanocobalamin,
0.001–0.05 g of choline dihydrogen citrate,
0.1–0.4 g of glycine,
0.1–0.5 g of L-valine,
0.1–0.5 g of L-lysine hydrochloride,
0.1–0.5 g of L-leucine,
0.1–0.5 g of L-isoleucine,
0.1–0.5 g of L-threonine,
0.02–0.05 g of L-tryptophan,
0.05–0.3 g of L-tyrosine,
0.15–0.25 g of L-arginine,
0.025–0.2 g of L-histidine,
0.1–0.5 g of L-cystine,
0.01–0.2 g of L-methionine,
0.1–0.5 g of L-proline,
0.1–0.4 g of L-phenylalanine,
0.05–0.5 g of L-asparagine,
0.01–0.1 g of L-serine,
0.01–0.1 g of L-alanine,
0.1–1.0 g of L-glutamic acid,
0.1–1.0 g of magnesium glycerophosphate monohydrate,
0.05–0.5 g of calcium gluconate,
0.4–2.0 g of anhydrous potassium dihydrogen phosphate,
1.0–4.0 g of anhydrous D-glucose, and
0.25–2.0 g of sodium citrate dihydrate.
(B) applying an amount of a therapeutically active substance
(C) incubating the nutrient medium and
(D) determining the activity of the therapeutically active substance by reference to the density in broth or the diameter of the inhibition zone.

* * * * *